United States Patent
Lee et al.

(10) Patent No.: US 9,759,675 B2
(45) Date of Patent: Sep. 12, 2017

(54) PARTICULATE MATTER SENSOR UNIT

(71) Applicants: Hyundai Motor Company, Seoul (KR); Kia Motors Corporation, Seoul (KR); SNU R&DB FOUNDATION, Seoul (KR)

(72) Inventors: Jin Ha Lee, Seoul (KR); Ji Ho Cho, Yongin-si (KR); Kukjin Chun, Seoul (KR); Sungchan Kang, Seoul (KR); Keunho Jang, Yongin-si (KR)

(73) Assignees: Hyundai Motor Company, Seoul (KR); Kia Motors Corporation, Seoul (KR); SNU R&DB FOUNDATION, Seoul (KR)

( * ) Notice: Subject to any disclaimer, the term of this patent is extended or adjusted under 35 U.S.C. 154(b) by 484 days.

(21) Appl. No.: 14/455,777

(22) Filed: Aug. 8, 2014

(65) Prior Publication Data

US 2014/0345362 A1 Nov. 27, 2014

Related U.S. Application Data

(62) Division of application No. 13/529,892, filed on Jun. 21, 2012, now abandoned.

(30) Foreign Application Priority Data

Dec. 9, 2011 (KR) .................. 10-2011-0132255

(51) Int. Cl.
| | |
|---|---|
| *G01N 7/00* | (2006.01) |
| *G01N 27/02* | (2006.01) |
| *G01N 15/06* | (2006.01) |
| *G01N 33/00* | (2006.01) |

(52) U.S. Cl.
CPC ......... *G01N 27/02* (2013.01); *G01N 15/0656* (2013.01); *G01N 33/0027* (2013.01); *F01N 2560/05* (2013.01)

(58) Field of Classification Search
CPC ............ G01M 15/102; G01N 15/0656; G01N 1/2252; G01N 33/0036; F01N 13/008
USPC .... 73/28.01, 23.31, 23.4, 35.16, 462, 114.71
See application file for complete search history.

(56) References Cited

U.S. PATENT DOCUMENTS

| | | | |
|---|---|---|---|
| 4,210,949 A | 7/1980 | Masuda | |
| 4,456,883 A * | 6/1984 | Bullis | F02D 41/1466 |
| | | | 324/130 |
| 6,719,950 B2 * | 4/2004 | Day | G01N 27/4071 |
| | | | 204/193 |

(Continued)

FOREIGN PATENT DOCUMENTS

| | | |
|---|---|---|
| CN | 101173865 A | 5/2008 |
| CN | 101216372 A | 7/2008 |

(Continued)

*Primary Examiner* — Eric S McCall
*Assistant Examiner* — Mohammed E Keramet-Amircola
(74) *Attorney, Agent, or Firm* — Morgan, Lewis & Bockius LLP

(57) ABSTRACT

A particulate matter (PM) sensor unit may include an exhaust line where exhaust gas passes, and a PM sensor that may be disposed at one side of the exhaust line and that generates a signal when particulate matter included in the exhaust gas passes the vicinity thereof, wherein the PM sensor may be an electrostatic induction type that generates an induction charge while the particulate matter having an electric charge passes the vicinity thereof.

6 Claims, 13 Drawing Sheets

(56) References Cited

U.S. PATENT DOCUMENTS

| | | | |
|---|---|---|---|
| 7,350,397 B2 | 4/2008 | Pidria et al. | |
| 8,047,051 B2* | 11/2011 | McCauley | G01N 27/4078 |
| | | | 73/23.31 |
| 8,047,054 B2 | 11/2011 | Below | |
| 8,215,153 B2* | 7/2012 | Matsubara | G01N 27/4077 |
| | | | 73/23.31 |
| 2005/0275772 A1 | 12/2005 | Oya et al. | |
| 2006/0121800 A1 | 6/2006 | Weyl et al. | |
| 2006/0277972 A1 | 12/2006 | Chand et al. | |
| 2007/0017285 A1* | 1/2007 | Wang | G01F 1/68 |
| | | | 73/204.26 |
| 2008/0028855 A1 | 2/2008 | Kano et al. | |
| 2008/0131991 A1* | 6/2008 | Kim | H01L 27/14687 |
| | | | 438/70 |
| 2008/0134753 A1* | 6/2008 | Jun | G01N 27/128 |
| | | | 73/23.2 |
| 2009/0188300 A1 | 7/2009 | Gualtieri et al. | |
| 2009/0241521 A1* | 10/2009 | Kim | B01D 53/9418 |
| | | | 60/295 |
| 2010/0005877 A1* | 1/2010 | Abe | B81B 7/0012 |
| | | | 73/204.26 |
| 2010/0147070 A1* | 6/2010 | Jun | G01N 27/121 |
| | | | 73/335.05 |
| 2010/0192670 A1 | 8/2010 | Schaenzlin et al. | |
| 2010/0229629 A1* | 9/2010 | Egami | G01N 15/0656 |
| | | | 73/28.01 |
| 2011/0107815 A1 | 5/2011 | Nelson et al. | |
| 2011/0265551 A1* | 11/2011 | Hopka | F01N 3/021 |
| | | | 73/23.31 |
| 2011/0283773 A1* | 11/2011 | Suzuki | G01K 7/16 |
| | | | 73/25.05 |
| 2012/0210769 A1* | 8/2012 | Roper | G01N 33/2847 |
| | | | 73/23.31 |
| 2013/0000283 A1* | 1/2013 | Lee | F01N 3/023 |
| | | | 60/297 |
| 2013/0036793 A1 | 2/2013 | White et al. | |

FOREIGN PATENT DOCUMENTS

| | | |
|---|---|---|
| CN | 102272571 A | 12/2011 |
| CN | 102338732 A | 2/2012 |
| JP | 54-40369 A | 3/1979 |
| JP | 59-94061 A | 5/1984 |
| JP | 60-154079 A | 8/1985 |
| JP | 2003-57200 A | 2/2003 |
| JP | 2003-098136 A | 4/2003 |
| JP | 2003-315193 A | 11/2003 |
| JP | 2005-10083 A | 1/2005 |
| JP | 2005-570710 A | 4/2005 |
| JP | 2010-210539 A | 9/2010 |
| JP | 2010-286412 A | 12/2010 |
| JP | 2011-153582 A | 8/2011 |
| JP | 2011-153930 A | 8/2011 |
| JP | 2011-169205 A | 9/2011 |
| JP | 2011-203093 A | 10/2011 |
| JP | 2011-247650 A | 12/2011 |

\* cited by examiner

- XY Plane

- XZ Plane

- YZ Plane

A - A'

A - A'

B - B'

A - A'

B - B'

PARTICULATE MATTER SENSOR UNIT

CROSS-REFERENCE TO RELATED APPLICATION

The present application is a Divisional of U.S. patent application Ser. No. 13/529,892, filed Jun. 21, 2012, which claims priority to Korean Patent Application No. 10-2011-0132255 filed in the Korean Intellectual Property Office on Dec. 9, 2011, the entire contents of which applications are incorporated herein for all purposes by this reference.

BACKGROUND OF THE INVENTION

Field of the Invention

The present invention relates to a particulate matter sensor unit that accurately and effectively detects damage to a particulate filter filtering particulate matter (PM) included in exhaust gas and transmits the detected signal to a control portion.

Description of Related Art

A diesel particulate filter (DPF) has been being applied to a diesel vehicle so as to reduce PM thereof, and a pressure difference sensor is applied to detect a PM amount that is trapped in the diesel particulate filter.

In the future, a pressure difference sensor will not be used to detect damage to the DPF according to exhaust gas regulations, and further, the detection precision of the pressure difference sensor is low.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a particulate matter sensor unit having advantages of accurately detecting an amount of PM (particulate matter) that is exhausted from a particulate filter and accurately detecting damage of the particulate filter through the detected PM amount.

In an aspect of the present invention, a particulate matter (PM) sensor unit, may include an exhaust line where exhaust gas passes, and a PM sensor that is disposed at one side of the exhaust line and that generates a signal when particulate matter may included in the exhaust gas passes the vicinity thereof, wherein the PM sensor is an electrostatic induction type that generates an induction charge while the particulate matter having an electric charge passes the vicinity thereof.

The PM sensor may include protrusions that protrude on a front surface portion of the PM sensor and are arranged with a predetermined width gap and a predetermined length gap therebetween, a heater electrode that is formed on a rear surface portion thereof to generate heat through a supplied current and that burns the particulate matter attached to the front surface portion, and a sensing electrode pad that is formed adjacent to the heater electrode to transmit the signal to the outside.

The heater electrode may include a portion that is formed as a zigzag shape.

The PM sensor may include a silicone electrode layer, and an insulating layer that is formed on a front surface portion and a rear surface portion of the silicone electrode layer to cover the silicone electrode layer, wherein a protruding electrode is formed on the front surface portion of the silicone electrode layer corresponding to the protrusions, and the insulating layer may have a predetermined thickness to cover the protruding electrode.

The insulating layer is not formed on the rear surface portion of the silicone electrode layer where the sensing electrode pad is formed.

The insulating layer may include an oxide layer covering the silicone electrode layer, and a nitride layer covering the oxide layer.

The shape of the protrusion may have one shape of a cuboid, a regular hexahedron, a sphere, a triangular pyramid, a quadrangular pyramid, and a cone.

In another aspect of the present invention, a manufacturing method of a particulate matter sensor unit, may include cleaning a silicone electrode layer, forming an etching prevention layer on an entire front surface portion of the silicone electrode layer, eliminating a regular pattern from the etching prevention layer, etching a front surface portion of the silicone electrode layer through the eliminated portion of the etching prevention layer to a predetermined depth, forming a protruding electrode by eliminating the etching prevention layer, forming an insulation layer on an entire front surface portion and rear surface portion to cover the protruding electrode, selectively eliminating a part where a sensing electrode pad is formed in the insulating layer that is formed on the rear surface portion of the silicone electrode layer, forming a PR layer of which a patterned part thereof is eliminated corresponding to a heat electrode on the entire rear surface portion of the silicone electrode layer, forming a Pt layer on the PR layer and the silicone electrode layer, and forming the sensing electrode pad and the heater electrode that are formed by the Pt layer on the silicone electrode layer by eliminating the PR layer.

The etching prevention layer is formed by deposing a TEOS component or sputtering Al.

When the predetermined pattern is eliminated from the etching prevention layer, a patterned mask is used to selectively expose the etching prevention layer to light, and the exposed part is eliminated with an etchant.

The forming the insulation layer sequentially forms an oxide layer and a nitride layer on the entire front surface portion and rear surface portion of the silicone electrode layer.

A part where the patterned part of the PR layer is eliminated may have a negative slope in the forming a PR layer.

The Pt layer may have a Pt component in the forming the Pt layer.

In an exemplary embodiment of the present invention, the amount of PM that is trapped in a diesel particulate filter (DPF) or particulate matter included in exhaust gas are accurately estimated to effectively cope with reinforced exhaust gas regulations.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
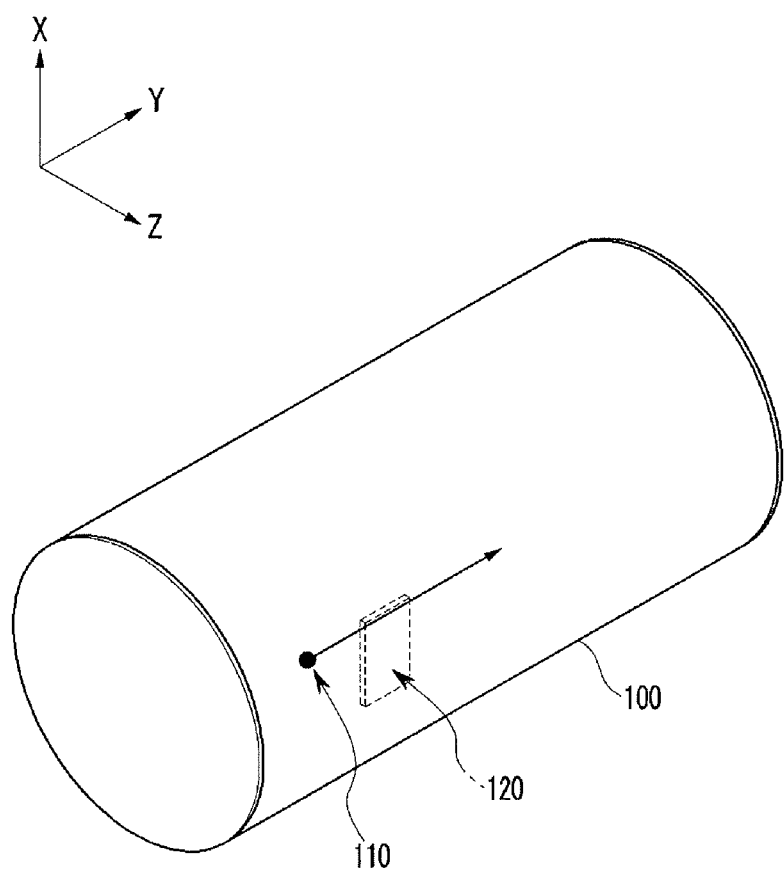
FIG. 1 is a schematic interior perspective view showing a condition that a particulate matter sensor unit is disposed in an exhaust line according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

An exemplary embodiment of the present invention will hereinafter be described in detail with reference to the accompanying drawings.

Figure 2A:
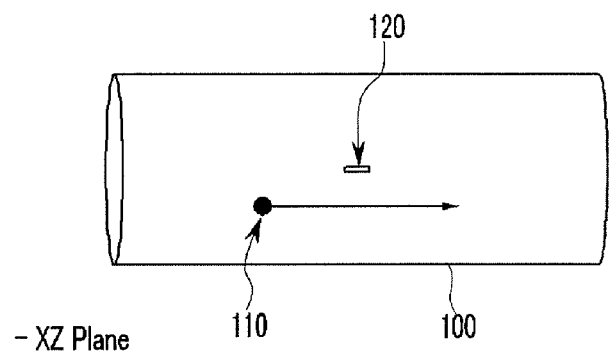
FIG. 2A is a plane view, a side view, and a front view showing a condition that a particulate matter sensor unit is disposed in an exhaust line according to an exemplary embodiment of the present invention.
Figure 2B:
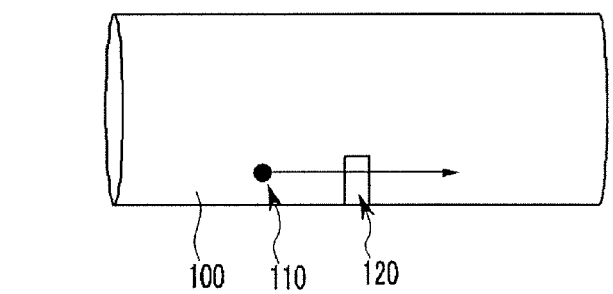
FIG. 2B is a plane view, a side view, and a front view showing a condition that a particulate matter sensor unit is disposed in an exhaust line according to an exemplary embodiment of the present invention.
Figure 2C:
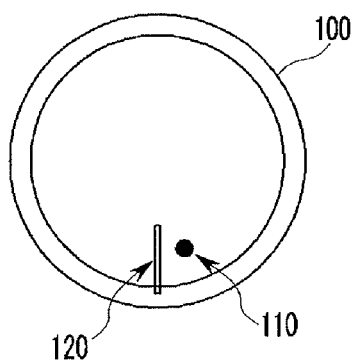
FIG. 2C is a plane view, a side view, and a front view showing a condition that a particulate matter sensor unit is disposed in an exhaust line according to an exemplary embodiment of the present invention.

FIG. 1 is a schematic interior perspective view showing a condition that a particulate matter sensor unit is disposed in an exhaust line according to an exemplary embodiment of the present invention, and FIG. 2 is a plane view, a side view, and a front view showing a condition that a particulate matter sensor unit is disposed in an exhaust line according to an exemplary embodiment of the present invention.

Referring to FIG. 1 and FIG. 2, exhaust gas flows in an exhaust line 100, and particulate matter 110 is included in the exhaust gas.

The particulate matter 110 passes the surroundings of a particulate matter (PM) sensor, and the PM sensor 120 generates a signal while the particulate matter 110 is passing.

The signal that is generated by the PM sensor 120 through an electric charge that is induced by the PM sensor 120.

Generally, the electric field that is generated by the charged particle is shown as the following equation.

$$\overline{E} = \frac{Q}{4\pi\varepsilon_0 r^2} \overline{u}_r$$

The Q is a charge amount that the charged particle has, and the r is a distance to the charged particle. Also, $\varepsilon_0$ is a dielectric constant in a vacuum condition.

A surface electric charge equal to the electric field that is formed by the charged particle matter is formed on the sensor electrode interface. The induced charge is determined by Laplace's equation. On a conductor plane plate that is disposed on a plane surface of which Z is 0 as a rectangular coordinate, when an electric charge having a charge amount Q is disposed on (0,0,d) coordinates, a potential and a surface electric charge density that are induced by a point electric charge is shown as the following equation.

$$V(x, y, z) = \frac{Q}{4\pi\varepsilon_0} \left[ \frac{1}{\sqrt{x^2 - y^2(z-d)^2}} - \frac{1}{\sqrt{x^2 - y^2 - (z-d)^2}} \right]$$

A potential that is generated by a point electric charge $$\overline{E} = -\nabla V$$
$$= \frac{Q}{4\pi\varepsilon_0} \left[ \frac{x \cdot \overline{a_x} + y \cdot \overline{a_y} + (z-d) \cdot \overline{a_z}}{(x^2 + y^2 - (z-d)^2)^{3/2}} - \frac{x \cdot \overline{a_x} - y \cdot \overline{a_y} - (z-d) \cdot \overline{a_z}}{(x^2 - y^2 + (z+d)^2)^{3/2}} \right]$$

An electric field that is generated by a point electric charge $$\rho = \varepsilon_0 E_z |_{z=0} = -\frac{Qd}{2\pi(x^2 + y^2 + d^2)^{3/2}}$$

A surface electric charge density that is induced $\bar{a}_x$, $\bar{a}_y$, $\bar{a}_z$ denote unit vectors of axis X, axis Y, and axis Z in rectangular coordinates.

Figure 13:
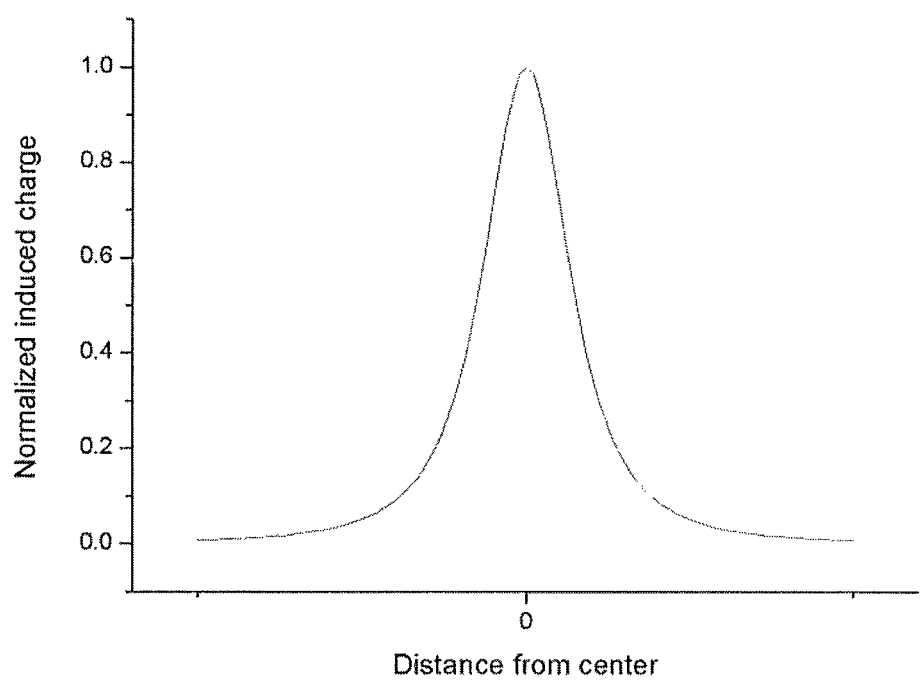
FIG. 13 is a graph showing normalized induced charge according to a distance between the charged particle and the electrode.

If the induced charge amount that is formed on a sensing electrode by the charged particle is displayed along axis X, a positive signal is formed as in FIG. 13 according to a distance between the charged particle and the electrode, which graph depicts an electric charge signal graph that is induced according to a distance X.

Figure 3:
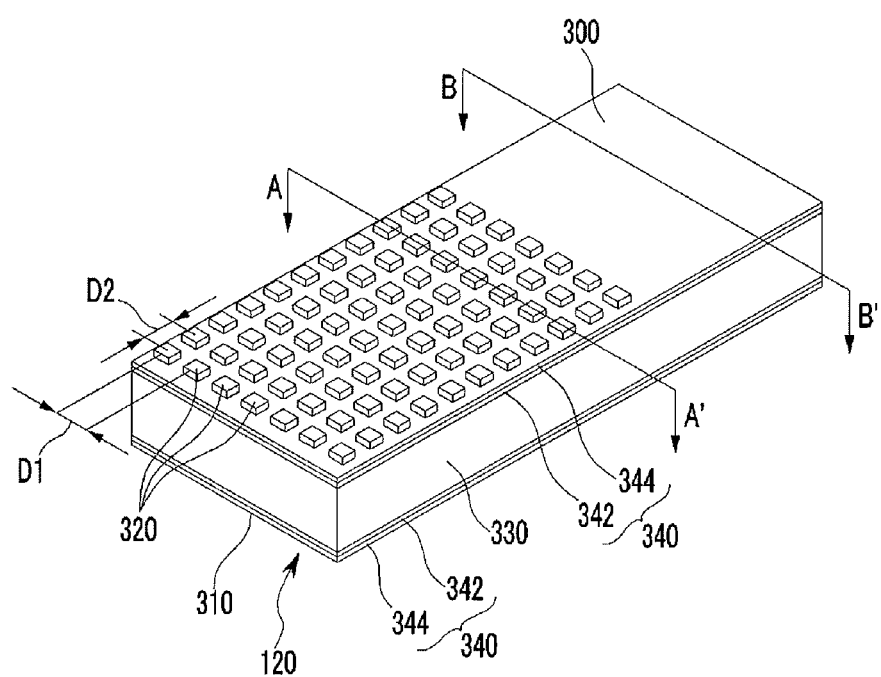
FIG. 3 is a perspective view showing a front side of a particulate matter sensor unit that is disposed in an exhaust line according to an exemplary embodiment of the present invention.

FIG. 3 is a perspective view showing a front side of a particulate matter sensor unit that is disposed in an exhaust line according to an exemplary embodiment of the present invention.

Referring to FIG. 3, the PM sensor 120 includes a silicone electrode layer 330 and an insulating layer 340.

The silicone electrode layer 330 is formed in a middle portion with a predetermined thickness, and the insulating layer 340 is thinly formed on a front surface portion 300 and a rear surface portion 310 of the silicone electrode layer 330.

The insulating layer 340 includes an oxide layer 342 that is formed on the silicone electrode layer 330 and a nitride layer 344 that is formed on the oxide layer 342.

Protrusions 320 having a quadrangle shape are formed on the front surface portion 300 of the PM sensor 120, wherein the protrusions 320 are formed at a first distance D1 in a width direction and a second distance D2 in a length direction.

In an exemplary embodiment of the present invention, the shape of the protrusions 320 can have at least a portion of one of a cuboid, a hexahedron, a sphere, a triangular pyramid, a quadrangular pyramid, and a circular cone, and the first distance D1 and the second distance D2 can be varied according to design specifications.

Figure 4:
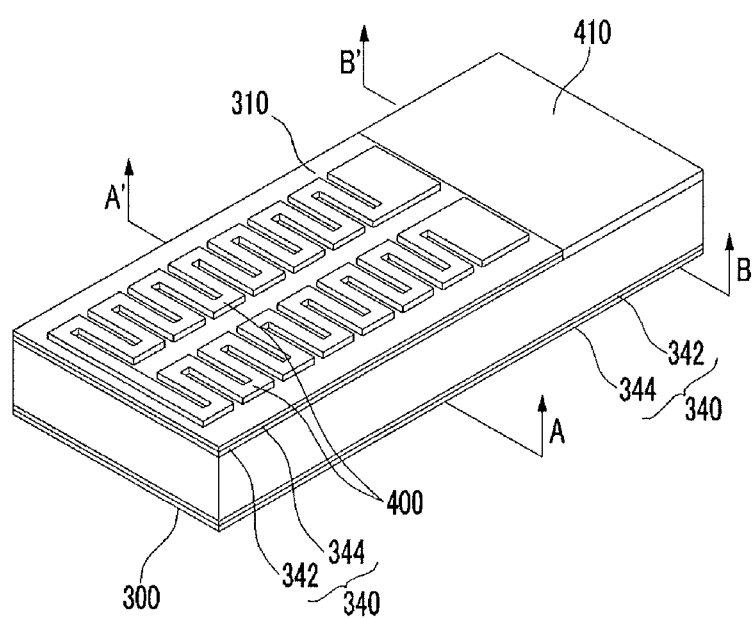
FIG. 4 is a perspective view showing a rear side of a particulate matter sensor unit that is disposed in an exhaust line according to an exemplary embodiment of the present invention.

Further, the height of the protrusions 320 can be variably applied according to design specifications. Referring to FIG. 4, the rear surface portion 310 of the PM sensor 120 will be described.

FIG. 4 is a perspective view showing a rear side of a particulate matter sensor unit that is disposed in an exhaust line according to an exemplary embodiment of the present invention.

Referring to FIG. 4, the insulating layer 340 is formed at one side of the rear surface portion of the PM sensor 120 and is not formed at the other side.

A heater electrode 400 is formed on the insulating layer 340, and as shown, the heater electrode 400 includes a part having a zigzag shape.

A sensing electrode pad 410 is formed on a part where the insulating layer 340 is not formed, and is electrically connected to the silicone electrode layer 330.

In an exemplary embodiment of the present invention, the silicone electrode layer 330 includes a Si component similar to a silicone wafer, and the heater electrode 400 and the sensing electrode pad 410 include platinum (Pt) that transfers electricity well and that has high durability.

Figure 5:
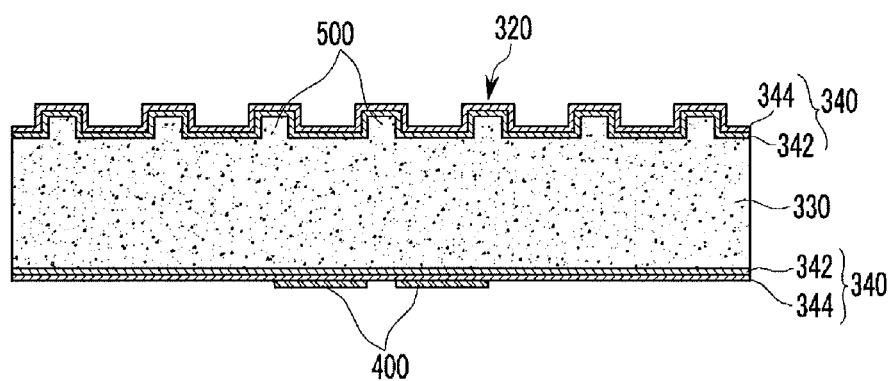
FIG. 5 is a cross-sectional view of a particulate matter sensor unit that is formed along line A-A' of FIG. 3.

FIG. 5 is a cross-sectional view of a particulate matter sensor unit that is formed along line A-A' of FIG. 3.

Referring to FIG. 5, a protruding electrode 500 is formed on the silicone electrode layer 330 corresponding to the protrusion 320. The insulating layer 340 is formed to cover the entire surface of the protruding electrode 500 and the silicone electrode layer 330.

As shown, the protruding electrode 500 that is formed on the silicone electrode layer 330 improves the sensitivity of the particulate matter. Further, the heater electrode 400 is formed on the insulating layer 340 at the rear surface portion of the PM sensor 120.

Figure 6:
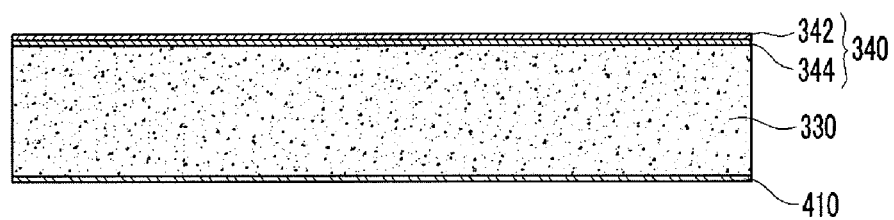
FIG. 6 is a cross-sectional view of a particulate matter sensor unit that is formed along line B-B' of FIG. 3.

FIG. 6 is a cross-sectional view of a particulate matter sensor unit that is formed along line B-B' of FIG. 3.

Referring to FIG. 6, the protruding electrode 500 is not formed at a part where the protrusion 320 is not formed on the silicone electrode layer 330, and the insulating layer 340 covers the part.

Further, the sensing electrode pad 410 that is directly electrically connected to the silicone electrode layer 330 is formed on a part where the insulating layer 340 is not formed at the rear surface portion of the PM sensor 120.

Figure 10A:
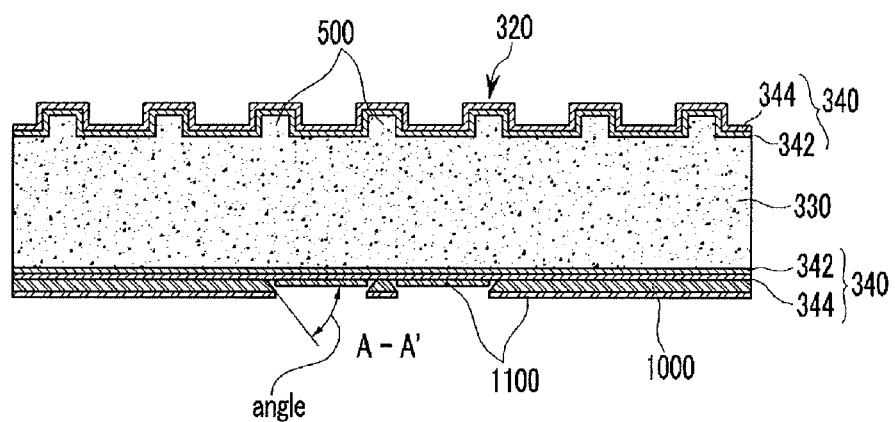
FIGS. 10A-10B are cross-sectional views that are formed along line A-A' and line B-B' showing manufacturing procedures of a particulate matter sensor unit according to an exemplary embodiment of the present invention.
Figure 10B:
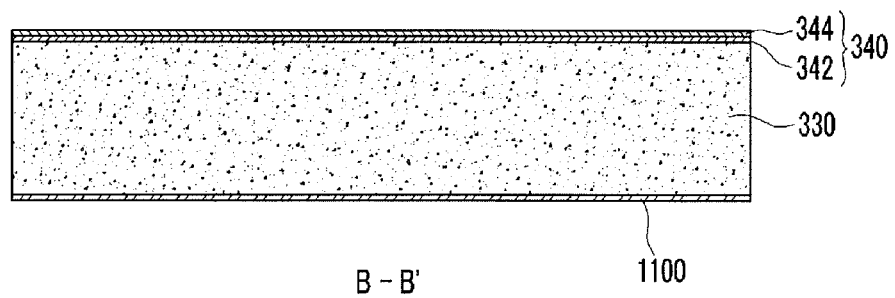
Figure 11A:
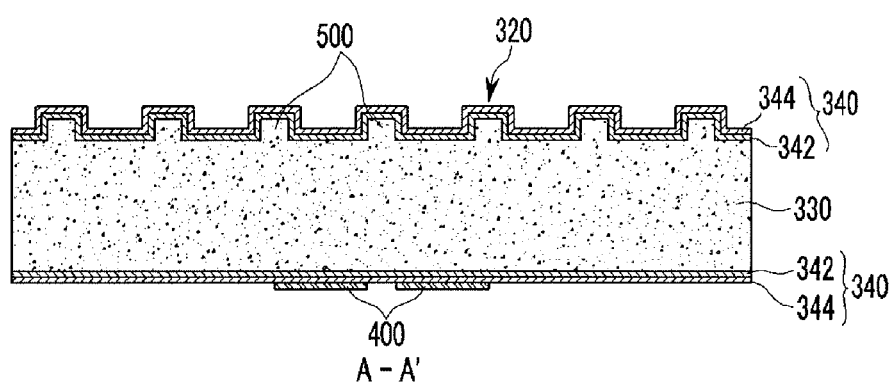
FIGS. 11A-11B are cross-sectional views that are formed along line A-A' and line B-B' showing manufacturing procedures of a particulate matter sensor unit according to an exemplary embodiment of the present invention.
Figure 11B:
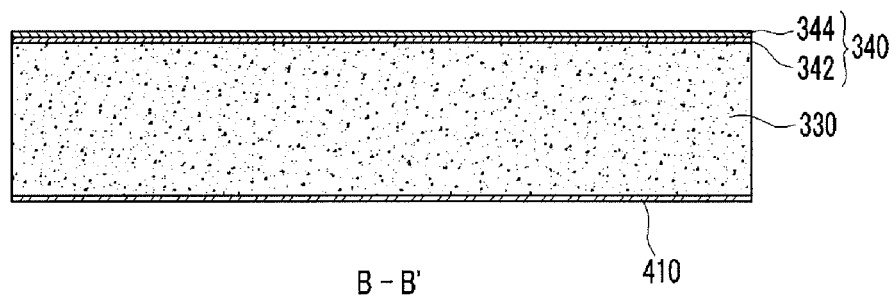
Figure 12:
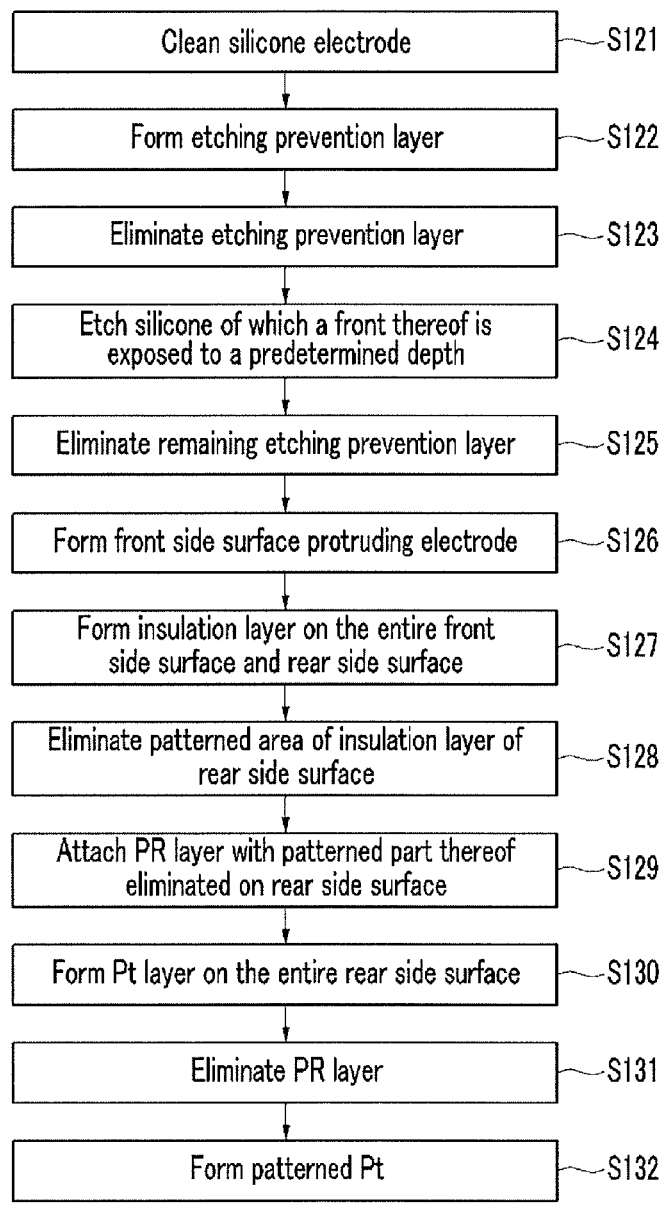
FIG. 12 is a flowchart showing a manufacturing procedure of a particulate matter sensor unit according to an exemplary embodiment of the present invention.

FIG. 7, FIG. 8, FIG. 9, FIG. 10, and FIG. 11 are cross-sectional views that are formed along line A-A' and line B-B' showing manufacturing procedures of a particulate matter sensor unit according to an exemplary embodiment of the present invention, and FIG. 12 is a flowchart showing a manufacturing procedure of a particulate matter sensor unit according to an exemplary embodiment of the present invention.

Firstly, referring to FIG. 12, the silicone electrode layer 330 is cleaned in step S121.

An etching prevention layer 700 is formed on the silicone electrode layer 330 in step S122, and the pattern of the etching prevention layer 700 is eliminated in step S123. Further, after the etching prevention layer 700 is removed, the exposed part of the silicone electrode layer 330 is etched in step S124.

The remaining etching prevention layer 700 is removed in step S125, and the protruding electrode 500 is formed on the front surface portion in step S126.

Figure 7:
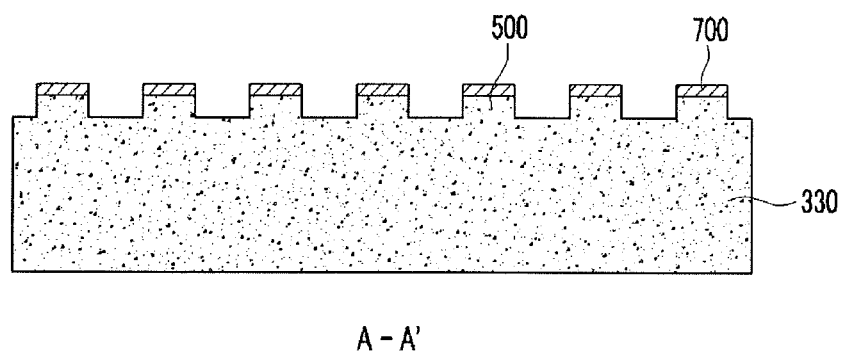
FIG. 7 is a cross-sectional view that is formed along line A-A' and line B-B' showing manufacturing procedures of a particulate matter sensor unit according to an exemplary embodiment of the present invention.

In a related step, referring to FIG. 7, the etching prevention layer 700 is formed on the silicone electrode layer 330, the etching prevention layer 700 is removed except the part corresponding to the protrusion 320, and the part where the etching prevention layer 700 is removed is etched to form the protruding electrode 500 on the silicone electrode layer 330.

Further, the etching prevention layer 700 that is disposed on the protruding electrode 500 is removed.

The insulating layer is formed on the entire front surface portion and rear surface portion of the silicone electrode layer in step S127.

Figure 8A:
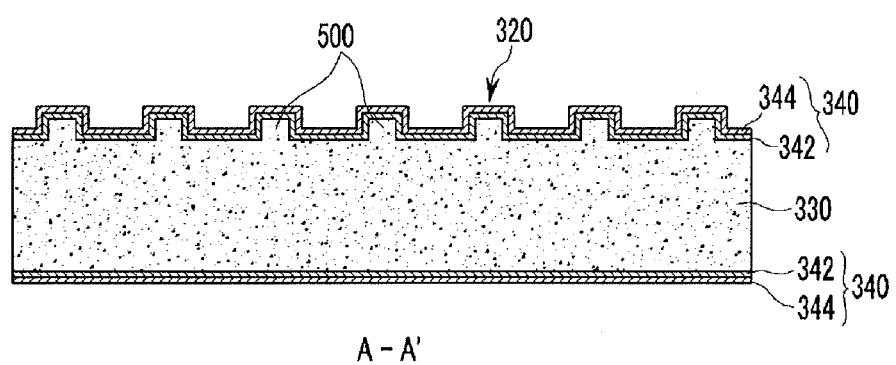
FIGS. 8A-8B are cross-sectional views that are formed along line A-A' and line B-B' showing manufacturing procedures of a particulate matter sensor unit according to an exemplary embodiment of the present invention.
Figure 8B:
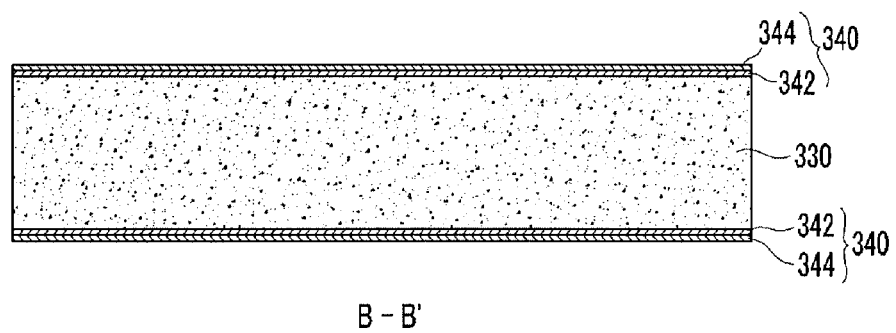

In a related step, referring to FIG. 8, the insulating layer 340 is formed on the front surface portion to cover the entire protruding electrode 500 and the other side of the silicone electrode layer 330, and the insulating layer 340 is formed on the rear surface portion.

A predetermined area of the insulating layer 340 that is formed on the rear surface portion of the silicone electrode layer 330 is removed in step S128. The removed part corresponds to the sensing electrode pad 410.

Figure 9A:
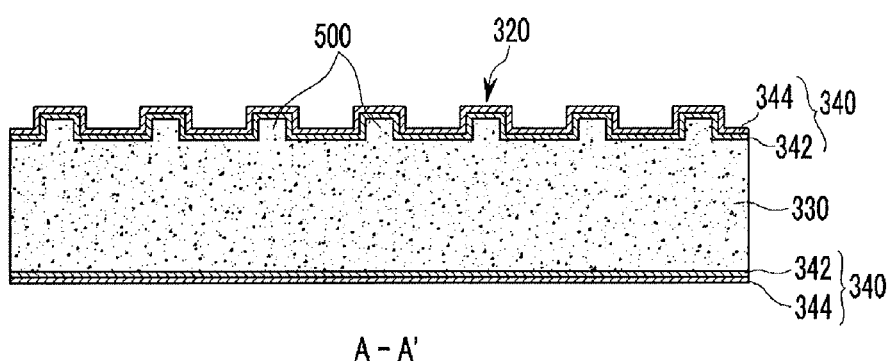
FIGS. 9A-9B are cross-sectional views that are formed along line A-A' and line B-B' showing manufacturing procedures of a particulate matter sensor unit according to an exemplary embodiment of the present invention.
Figure 9B:
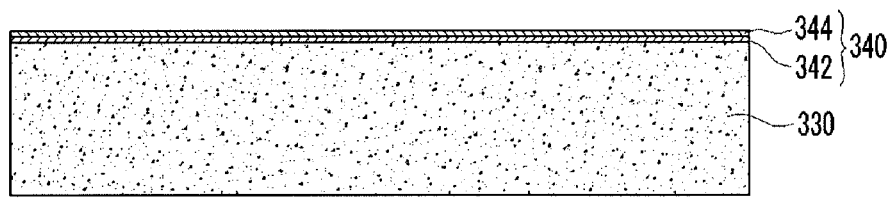

In a related step, referring to FIG. 9, a part of the insulating layer 340 that is formed on a rear side surface of the silicone electrode layer 330 is removed such that a part of the rear side of the silicone electrode layer 330 is exposed.

A photoresist (PR) layer 1000 of which a patterned part thereof is removed is formed on the rear side surface in step S129. The part where the heater electrode 400 and the sensing electrode pad 410 are to be formed is removed from the PR layer 1000.

Further, a platinum (Pt) layer 1100 is formed on the entire rear side surface including the part where the PR layer 1000, is removed in step S130.

In a related step, referring to FIG. 10, the removed part of the PR layer 1000 has a negative slope. That is, an angle that the removed part of the PR layer 1000 forms with the insulating layer 340 is within 90 degrees.

Further, the Pt layer 1100 is formed on the entire rear side surface and on the insulating layer 340 at the part where the PR layer 1000 is not formed. Then, the PR layer 1000 is removed in step S131.

In a related step, referring to FIG. 10 and FIG. 11, if the PR layer 1000 is removed from the rear surface portion, the Pt layer 1100 that is attached on the insulating layer 340 is maintained, in step S132. Accordingly, only the heater electrode 400 and the sensing electrode pad 410 are maintained on the rear surface portion of the PM sensor 120.

In an exemplary embodiment of the present invention, one of the layers can be formed by sputtering, deposition, or etching, and a film and a pattern thereof can be removed by a photoresist method using a mask. Further, an etchant is used to etch or peel a predetermined area.

For convenience in explanation and accurate definition in the appended claims, the terms "upper", "lower", "inner" and "outer" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A manufacturing method of a particulate matter sensor unit, comprising:
    cleaning a silicone electrode layer;
    forming an etching prevention layer on an entire front surface portion of the silicone electrode layer;
    eliminating a regular pattern from the etching prevention layer;
    etching a front surface portion of the silicone electrode layer through the eliminated portion of the etching prevention layer to a predetermined depth;
    forming a protruding electrode by eliminating the etching prevention layer;
    forming an insulation layer on an entire front surface portion and rear surface portion to cover the protruding electrode;
    selectively eliminating a part where a sensing electrode pad is formed in the insulating layer formed on the rear surface portion of the silicone electrode layer;
    forming a PR layer of which a patterned part thereof is eliminated corresponding to a heat electrode on the entire rear surface portion of the silicone electrode layer;
    forming a Pt layer on the PR layer and the silicone electrode layer; and
    forming the sensing electrode pad and the heater electrode that are formed by the Pt layer on the silicone electrode layer by eliminating the PR layer.

2. The manufacturing method of claim 1, wherein the etching prevention layer is formed by deposing a TEOS component or sputtering Al.

3. The manufacturing method of claim 1, wherein when the predetermined pattern is eliminated from the etching prevention layer, a patterned mask is used to selectively expose the etching prevention layer to light, and the exposed part is eliminated with an etchant.

4. The manufacturing method of claim 1, wherein the forming the insulation layer sequentially forms an oxide layer and a nitride layer on the entire front surface portion and rear surface portion of the silicone electrode layer.

5. The manufacturing method of claim 1, wherein a part where the patterned part of the PR layer is eliminated has a negative slope in the forming a PR layer.

6. The manufacturing method of claim 1, wherein the Pt layer has a Pt component in the forming the Pt layer.

* * * * *